United States Patent
Young (10) Patent No.: US 8,221,412 B2
(45) Date of Patent: *Jul. 17, 2012

(54) MEDICAL NEEDLES AND ELECTRODES WITH IMPROVED BENDING STIFFNESS

(75) Inventor: Kimbolt Young, Newtonville, MA (US)

(73) Assignee: Boston Scientific Scimed, Inc., Maple Grove, MA (US)

( * ) Notice: Subject to any disclaimer, the term of this patent is extended or adjusted under 35 U.S.C. 154(b) by 90 days.

This patent is subject to a terminal disclaimer.

(21) Appl. No.: 12/693,273

(22) Filed: Jan. 25, 2010

(65) Prior Publication Data

US 2010/0125250 A1    May 20, 2010

Related U.S. Application Data

(63) Continuation of application No. 11/078,933, filed on Mar. 10, 2005, now Pat. No. 7,678,107.

(51) Int. Cl.
*A61B 18/12* (2006.01)
(52) U.S. Cl. ............. 606/41; 606/45; 606/48; 606/51
(58) Field of Classification Search .............. 606/41, 606/45, 48, 51
See application file for complete search history.

(56) References Cited

U.S. PATENT DOCUMENTS

| | | | |
|---|---|---|---|
| 2,830,587 A | 4/1958 | Everett | |
| 3,174,851 A | 3/1965 | Buehler et al. | |
| 3,351,463 A | 11/1967 | Rozner et al. | |
| 3,753,700 A | 8/1973 | Harrison et al. | |
| 5,075,062 A | 12/1991 | Karpiel | |
| 5,672,174 A | 9/1997 | Gough et al. | |
| 5,810,789 A | 9/1998 | Powers et al. | |
| 5,855,576 A | 1/1999 | LeVeen et al. | |
| 6,270,476 B1 | 8/2001 | Santoianni et al. | |

(Continued)

FOREIGN PATENT DOCUMENTS

EP    1 374 943 A1    1/2004

OTHER PUBLICATIONS

PCT International Search Report for PCT/US2006/007490, Applicant: Boston Scientific Scimed, Inc., Form PCT/ISA/210 and 220, dated Aug. 8, 2006 (6 pages).

(Continued)

*Primary Examiner* — Aaron Roane (74) *Attorney, Agent, or Firm* — Vista IP Lawgroup LLP (57) ABSTRACT

A device for penetrating tissue includes an elongated element having a distal end, a proximal end, a body extending between the distal and the proximal ends, and a lumen located within at least a portion of the body, wherein the lumen has a cross-sectional shape that is a polygon. A device for penetrating tissue includes an elongated element having a distal end, a proximal end, and a body extending between the distal and the proximal ends, at least a portion of the body having a cross-sectional profile that is a polygon, wherein the elongated element is a cannula.

15 Claims, 5 Drawing Sheets

U.S. PATENT DOCUMENTS

| | | | |
|---|---|---|---|
| 6,379,353 | B1 | 4/2002 | Nichols |
| 6,406,476 | B1 | 6/2002 | Kirwan, Jr. et al. |
| 6,443,669 | B2 | 9/2002 | Saito |
| 6,572,613 | B1 | 6/2003 | Ellman et al. |
| 2003/0109871 | A1 | 6/2003 | Johnson et al. |
| 2003/0195500 | A1* | 10/2003 | Moorman et al. ............ 606/33 |
| 2004/0059325 | A1 | 3/2004 | Swanson |
| 2004/0116848 | A1 | 6/2004 | Gardeski et al. |
| 2005/0070959 | A1 | 3/2005 | Cichocki et al. |

OTHER PUBLICATIONS

PCT Written Opinion of the International Search Authority for PCT/US2006/007490, Applicant: Boston Scientific Scimed, Inc., Form PCT/ISA/237, dated Aug. 8, 2006 (6 pages).

PCT International Preliminary Report on Patentability (Chapter I of the Patent Cooperation Treaty) for PCT/US2006/007490, Applicant: Boston Scientific Scimed, Inc., Form PCT/IB/326 and 373, dated Sep. 12, 2007 (7 pages).

* cited by examiner

MEDICAL NEEDLES AND ELECTRODES WITH IMPROVED BENDING STIFFNESS

RELATED APPLICATION

This application is a continuation of U.S. patent application Ser. No. 11/078,933, filed on Mar. 10, 2005, issued as U.S. Pat. No. 7,678,107, the disclosures of which is expressly incorporated herein by reference.

FIELD OF THE INVENTION

The field of the invention relates generally to medical devices, and more particularly, to tissue-penetrating elements, such as electrodes and needles, and medical devices having such tissue-penetrating elements.

BACKGROUND OF THE INVENTION

Many existing medical devices includes tissue-penetrating elements. For example, U.S. Pat. No. 5,855,576 describes an ablation apparatus that includes a plurality of electrode tines (elongated electrodes) deployable from a cannula. Each of the tines includes a proximal end that is coupled to a generator, and a distal end that may project from a distal end of the cannula. When using the above described devices in percutaneous interventions, the cannula is generally inserted through a patient's skin to penetrate tissue, and the elongated electrodes are deployed out of the distal end of the cannula. The electrodes are then energized to ablate the target tissue.

It has been found that elongated electrodes have relatively low bending stiffness, thereby allowing the electrodes to easily bend during use. Sometimes, the bending of the electrodes may result in a deployed configuration of the electrodes within tissue that is not as that intended.

Also, sometimes it may be desirable to reposition the cannula and deploy the electrodes at a different location to create an additional lesion. For example, the cannula can be retracted and removed from the first target site, and reinserted into a new target site. However, such technique results in multiple puncture wounds and may increase the chance of metastasis resulted from cancer seeds migrating to other bodily locations through the puncture wounds. Sometimes, in order to minimize puncture wounds, a physician may attempt to turn or steer the distal end of the cannula (e.g., by applying a bending force at the proximal end of the cannula) to aim the distal end at different target tissue while the distal end is still inside the tissue. However, the cannula used to deploy the electrodes generally has relatively low bending stiffness, thereby preventing a physician from applying bending force at the proximal end of the cannula (e.g., applying a torque about an axis that is at an angle relative to an axis of the cannula).

Tissue-penetrating elements, such as medical needles, have also been used in a variety of applications. For examples, medical needles have been used to deliver substance, such as drug, contrast agent, diagnostic agent, and radioactive objects, to patients. Medical needles have also been used to collect substance, such as blood, tissue, or other bodily fluid, from a patient. In either case, the medical needle generally has a sharp distal tip for penetrating tissue, and is attached to a container in which the substance to be delivered or collected is stored. During use, the needle tip is used to pierce through a patient's skin to reach target site, and the substance is delivered to, or collected from, the target site via the needle. Sometimes, in order to minimize the size of the wound at the patient's skin, the needle is made to have a circular cross-section having a small cross-sectional diameter. However, a needle with such configuration can bend easily as it is advanced into a patient's body, thereby resulting in the needle tip being inaccurately positioned.

Thus, there remains a need to provide for improved tissue-penetrating elements, such as elongated electrodes and medical needles, with good bending stiffness.

SUMMARY OF THE INVENTION

In accordance with some embodiments, a device for penetrating tissue includes an elongated element having a distal end, a proximal end, a body extending between the distal and the proximal ends, and a lumen located within at least a portion of the body, wherein the lumen has a cross-sectional shape that is a polygon.

In accordance with other embodiments, a device for penetrating tissue includes an elongated element having a distal end, a proximal end, and a body extending between the distal and the proximal ends, at least a portion of the body having a cross-sectional profile that is a polygon, wherein the elongated element is a cannula.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments. It should be noted that the figures are not drawn to scale and that elements of similar structures or functions are represented by like reference numerals throughout the figures. Understanding that these drawings depict only typical embodiments of and are not therefore to be considered limiting of its scope, the embodiments will be described and explained with additional specificity and detail through the use of the accompanying drawings in which.

DETAILED DESCRIPTION OF THE EMBODIMENTS

Figure 1:
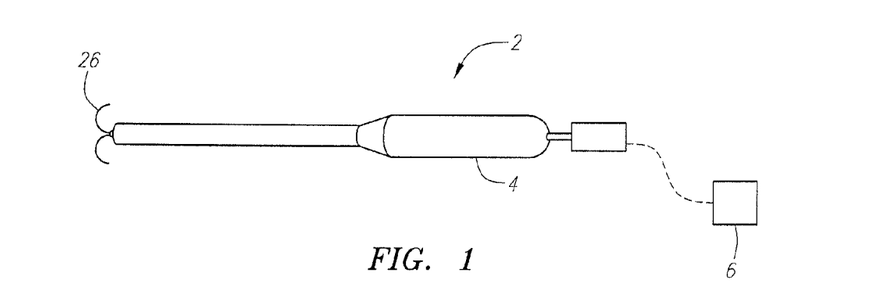
FIG. 1 is a schematic diagram of a tissue ablation system in accordance with some embodiments.

FIG. 1 illustrates a tissue ablation system 2 constructed in accordance with some embodiments of the invention. The tissue ablation system 2 includes a probe assembly 4 configured for introduction into the body of a patient for ablative treatment of target tissue, and a radio frequency (RF) generator 6 configured for supplying RF energy to the probe assembly 4 in a controlled manner.

Figure 2:
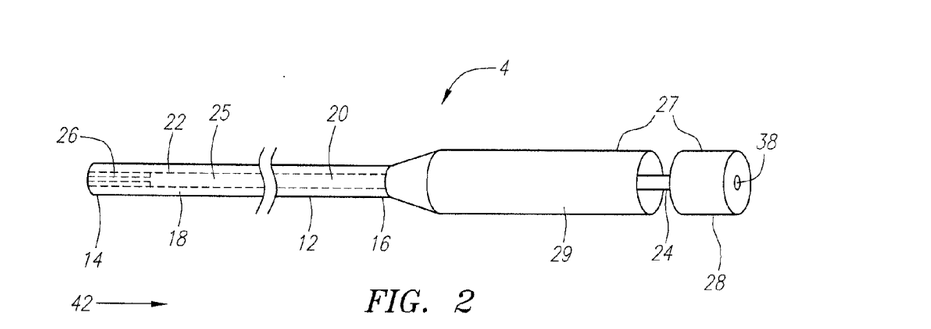
FIG. 2 is a perspective view of the ablation probe used in the system of FIG. 1, wherein an electrode array is particularly shown retracted.
Figure 3:
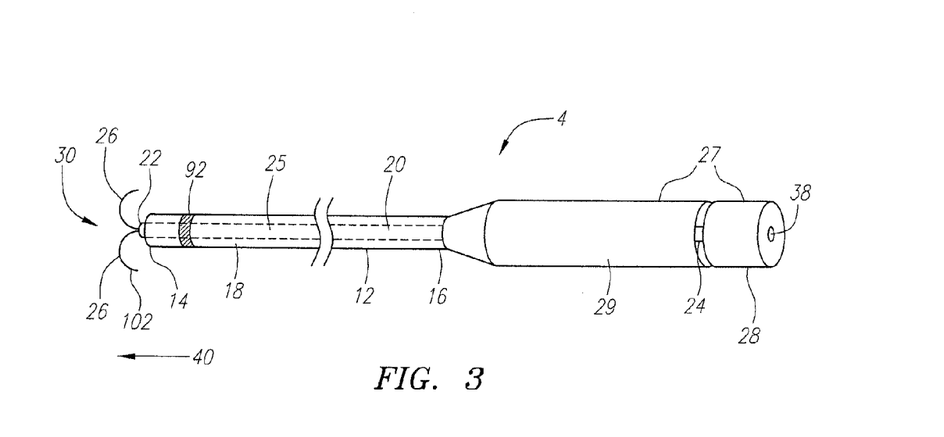
FIG. 3 is a perspective view of the ablation probe of FIG. 2, wherein an electrode array is particularly shown deployed.

Referring specifically now to FIGS. 2 and 3, the probe assembly 4 includes an elongate cannula 12, a shaft 20 slidably disposed within the cannula 12, and an array 30 of electrodes 26 carried by the shaft 20. The array 30 of electrodes 26 can be manufactured as a single component. As such, the "array of electrodes" should not be limited to a plurality of separate electrodes, and includes a single structure (e.g., an electrode) having different conductive portions. The cannula 12 has a distal end 14, a proximal end 16, and a central lumen 18 extending through the cannula 12 between the distal end 14 and the proximal end 16. The cannula 12 may be rigid, semi-rigid, or flexible depending upon the designed means for introducing the cannula 12 to the target tissue. The cannula 12 is composed of a suitable material, such as plastic, metal or the like, and has a suitable length, typically in the range from 5 cm to 30 cm, preferably from 10 cm to 20 cm. The length of the cannula 12 can also have other dimensions. If composed of an electrically conductive material, the cannula 12 is preferably covered with an insulative material. The cannula 12 has an outside cross sectional dimension consistent with its intended use, typically being from 0.5 mm to 5 mm, usually from 1.3 mm to 4 mm. The cannula 12 may have an inner cross sectional dimension in the range from 0.3 mm to 4 mm, preferably from 1 mm to 3.5 mm. The cannula 12 can also have other outside and inner cross sectional dimensions in other embodiments.

It can be appreciated that longitudinal translation of the shaft 20 relative to the cannula 12 in a distal direction 40 deploys the electrode tines 26 from the distal end 14 of the cannula 12 (FIG. 3), and longitudinal translation of the shaft 20 relative to the cannula 12 in a proximal direction 42 retracts the electrode tines 26 into the distal end 14 of the cannula 12 (FIG. 2). The shaft 20 comprises a distal end 22 and a proximal end 24. Like the cannula 12, the shaft 20 is composed of a suitable material, such as plastic, metal or the like.

In the illustrated embodiment, each electrode 26 takes the form of an electrode tine, which resembles the shape of a needle or wire. Each of the electrodes 26 is in the form of a slander metal element, which can penetrate into tissue as it is advanced from a target site within the target region. In some embodiments, distal ends 102 of the electrodes 26 may be honed or sharpened to facilitate their ability to penetrate tissue. The distal ends 102 of these electrodes 26 may be hardened using conventional heat treatment or other metallurgical processes. They may be partially covered with insulation, although they will be at least partially free from insulation over their distal portions.

When deployed from the cannula 12, the array 30 of electrodes 26 has a deployed configuration that defines a volume having a periphery with a radius in the range from 0.5 to 4 cm. However, in other embodiments, the radius can be other values. The electrodes 26 are resilient and pre-shaped to assume a desired configuration when advanced into tissue. In the illustrated embodiments, the electrodes 26 diverge radially outwardly from the cannula 12 in a uniform pattern, i.e., with the spacing between adjacent electrodes 26 diverging in a substantially uniform and/or symmetric pattern. The electrodes 26 should not be limited to having the profiles shown in FIG. 3, and that in alternative embodiments, the electrodes 26 can have different deployed profiles.

It should be noted that although a total of two electrodes 26 are illustrated in FIG. 3, in other embodiments, the probe assembly 4 can have more or fewer than two electrodes 26. In exemplary embodiments, pairs of adjacent electrodes 26 can be spaced from each other in similar or identical, repeated patterns and can be symmetrically positioned about an axis of the shaft 20. It will be appreciated that a wide variety of particular patterns can be provided to uniformly cover the region to be treated. In other embodiments, the electrodes 26 may be spaced from each other in a non-uniform pattern.

The electrodes 26 can be made from a variety of electrically conductive elastic materials. Very desirable materials of construction, from a mechanical point of view, are materials which maintain their shape despite being subjected to high stress. Certain "super-elastic alloys" include nickel/titanium alloys, copper/zinc alloys, or nickel/aluminum alloys. Alloys that may be used are also described in U.S. Pat. Nos. 3,174,851, 3,351,463, and 3,753,700, the disclosures of which are hereby expressly incorporated by reference. The electrodes 26 may also be made from any of a wide variety of stainless steels. The electrodes 26 may also include the Platinum Group metals, especially platinum, rhodium, palladium, rhenium, as well as tungsten, gold, silver, tantalum, and alloys of these metals. These metals are largely biologically inert. They also have significant radiopacity to allow the electrodes 26 to be visualized in-situ, and their alloys may be tailored to accomplish an appropriate blend of flexibility and stiffness. They may be coated onto the electrodes 26 or be mixed with another material used for construction of the electrodes 26.

Figures 4, 5, 6, 7, 8, 9:
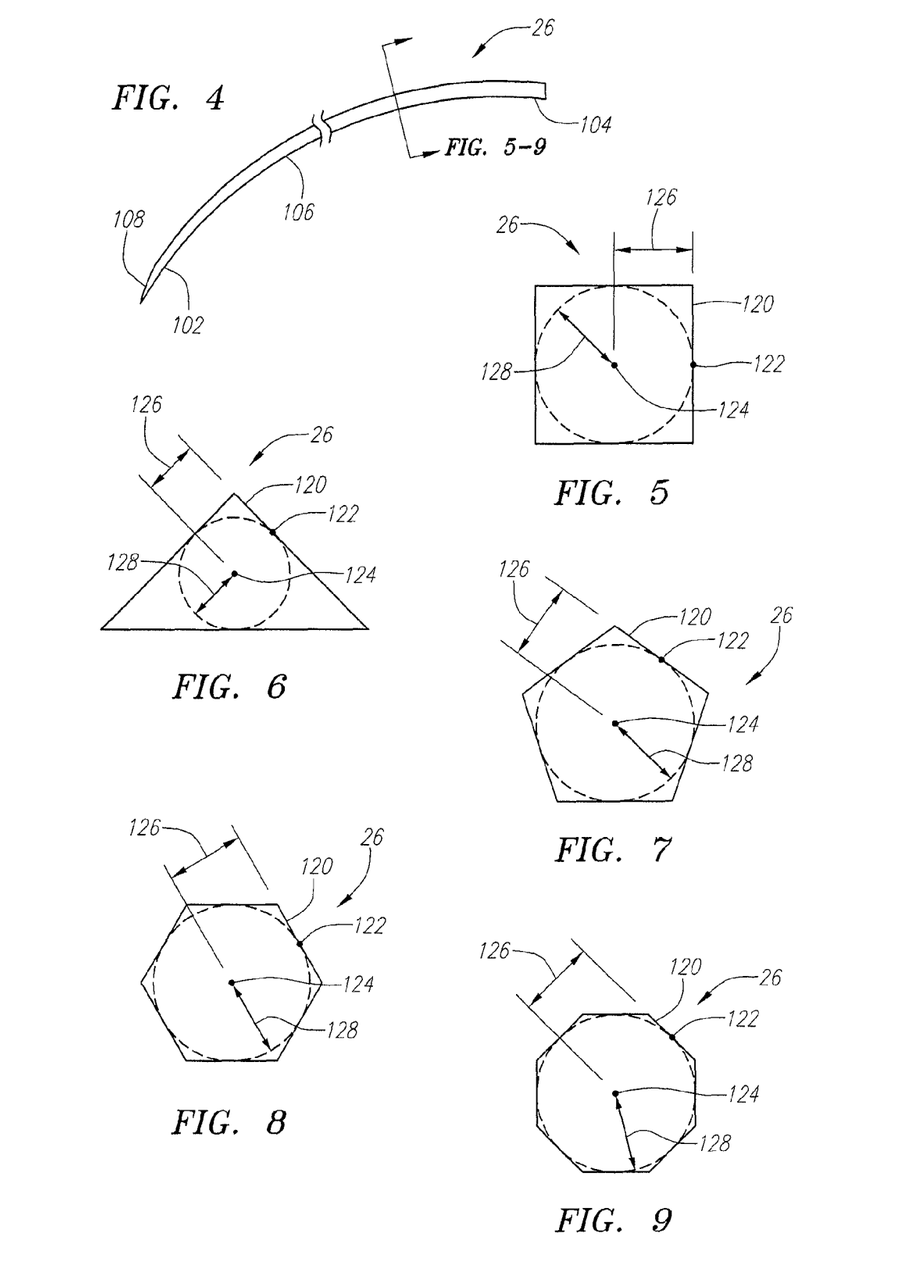
FIG. 4 illustrates a partial side cross-sectional view of the electrode of FIG. 2.
FIG. 5 illustrates a cross-sectional view of the electrode of FIG. 4.
FIGS. 6-9 illustrate alternative cross-sections of the electrode of FIG. 4.

Referring to FIG. 4, which illustrates a partial cross-sectional side view of the electrode 26 (tissue-penetrating element) constructed in accordance with some embodiments of the invention. The electrode 26 has a distal end 102, a proximal end 104, and a body 106 between the distal and the proximal ends 102, 104. The electrode 26 further includes a sharp distal tip 108 for penetrating tissue. As used in this specification, the term "tissue-penetrating element" is not limited to structures that have tissue piercing capability, and includes structures that do not have tissue piercing capability, as long as the structures are placeable or adapted to be placed at least partially within a body.

FIG. 5 illustrates a cross-sectional view of the electrode 26 of FIG. 4. As shown in FIG. 5, at least a portion of the body 106 of the electrode 26 has a square profile, with a plurality of sides 120. The body 106 is sized such that the sides 120 are tangential to a circle (shown in dotted lines) having a prescribed radius (or dimension) 128. Particularly, a distance 126 between a midpoint 122 on a side 120 and a center 124 of the square is equal to the prescribed dimension 128. In the illustrated embodiments, the prescribed dimension 128 can be any value between 0.01 cm to 0.5 cm, and more preferably, between 0.04 cm to 0.3 cm. The prescribed dimension 128 can be other values in other embodiments. The square cross-sectional profile/shape of the body 106 is advantageous over a circular cross-sectional profile (having radius equal to the prescribed dimension 128) in that, for a given prescribed dimension 128, the square cross-sectional profile provides better cross-sectional property (e.g., higher moment of inertia I), thereby resulting in the body 106 having a stronger bending stiffness than that of the circular cross-sectional profile.

In other embodiments, the body 106 can be sized such that the electrode 26 has a prescribed bending stiffness. For example, the body 106 can be sized to have a prescribed bending stiffness such that when the electrode 26 is deployed within tissue, the electrode 26 will substantially assume its intended delivery shape. The bending stiffness of the electrode 26 is a function of a moment of inertia (I) of the cross-section of the body 106. Generally, a cross-section of the electrode 26 with a higher moment of inertia will provide a higher bending stiffness for the electrode 26. A square cross-sectional profile sized to have a prescribed moment of inertia will have a smaller cross-sectional dimension (equal to two times the distance 126) than that of a circular cross-sectional profile sized to have the same prescribed moment of inertia. As such, the square cross-sectional profile is better than a circular cross-sectional profile in that, for a given material of construction, it can provide the prescribed bending stiffness for the electrode 26, while allowing the electrode 26 to be constructed with a smaller cross-sectional dimension.

It should be noted that in alternative embodiments, instead of a square profile, at least a portion of the electrode body 106 can have other cross-sectional profiles, such as a triangle (FIG. 6), a pentagon (FIG. 7), a hexagon (FIG. 8), and an octagon (FIG. 9). As similarly discussed previously, any of the polygon cross-sectional profiles illustrated in FIGS. 6-9 is advantageous over a circular cross-sectional profile. Also, in other embodiments, instead of having the deployed profile shown in FIG. 3, the electrode 26 can have a straight deployed profile, other deployed curvilinear profiles (such as an arc, or a bent), or other customized deployed profiles.

Returning to FIGS. 2 and 3, the probe assembly 4 further includes an electrode 92 secured to the cannula 12. The electrode 92 is operative in conjunction with the array 30 to deliver energy to tissue. The electrodes 26 in the array 30 are positive (or active) electrodes while the operative electrode 92 is a negative (or return) electrode for completing energy path(s). In such cases, energy is directed from the electrodes 26 in the array 30 radially inward towards the electrode 92. Alternatively, the electrode 92 can be active electrode while the electrodes 26 in the array 30 are return electrodes for completing energy path(s), in which cases, energy is directed from the electrode 92 radially outward towards the electrodes 26. In the illustrated embodiments, the operative electrode 92 has a tubular shape, but can have other shapes in alternative embodiments.

In the illustrated embodiments, the array 30 of electrodes 26 and the operative electrode 92 are used to deliver RF current in a bipolar fashion, which means that current will pass between the array 30 of electrodes 26 and the operative electrode 92. In a bipolar arrangement, the array 30 and the electrode 92 will be insulated from each other in any region(s) where they would or could be in contact with each other during a power delivery phase.

Alternatively, the RF current is delivered to the electrode array 30 in a monopolar fashion, which means that current will pass from the electrode array 30, which is configured to concentrate the energy flux in order to have an injurious effect on the surrounding tissue, and a dispersive electrode (not shown), which is located remotely from the electrode array 30 and has a sufficiently large area (typically 130 cm$^2$ for an adult), so that the current density is low and non-injurious to surrounding tissue. In such cases, the electrode assembly 4 does not include the operative electrode 92. The dispersive electrode may be attached externally to the patient, e.g., using a contact pad placed on the patient's flank.

The probe assembly 4 further includes a handle assembly 27, which includes a handle portion 28 mounted to the proximal end 24 of the shaft 20, and a handle body 29 mounted to the proximal end 16 of the cannula 12. The handle portion 28 is slidably engaged with the handle body 29 (and the cannula 20). The handle portion 28 also includes an electrical connector 38, which allows the probe assembly 2 to be connected to the generator 6 during use. The electrical connector 38 is electrically coupled to the electrodes 26. The electrical connector 38 can be conveniently coupled to the electrodes 26 via the shaft 20 (which will be electrically conductive), although in other embodiments, the connector 38 can be coupled to the electrodes 26 via separate wires (not shown). The handle portion 28 and the handle body 29 can be composed of any suitable rigid material, such as, e.g., metal, plastic, or the like.

Referring back to FIG. 1, the RF generator 6 is electrically connected to the electrical connector 38, which may be directly or indirectly (e.g., via a conductor) electrically coupled to the electrode array 30. The RF generator 6 is a conventional RF power supply that operates at a frequency in the range from 200 KHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for vessel occlusion. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., which markets these power supplies under the trademarks RF2000 (100 W) and RF3000 (200 W).

Figures 10A, 10B:
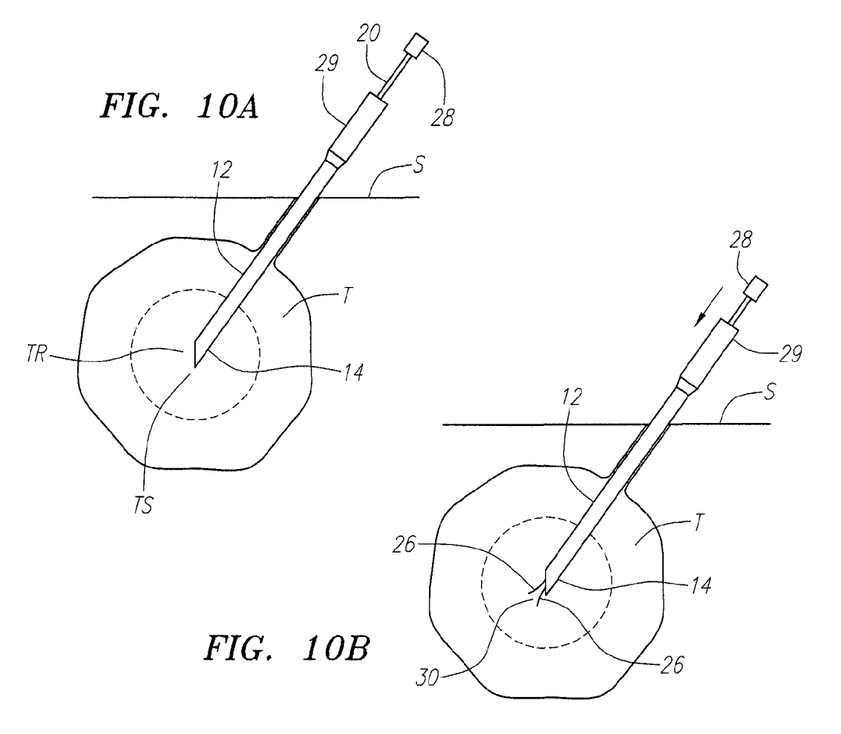
FIGS. 10A-10C are cross-sectional views, showing a method for treating tissue, in accordance with some embodiments.
Figure 10C:
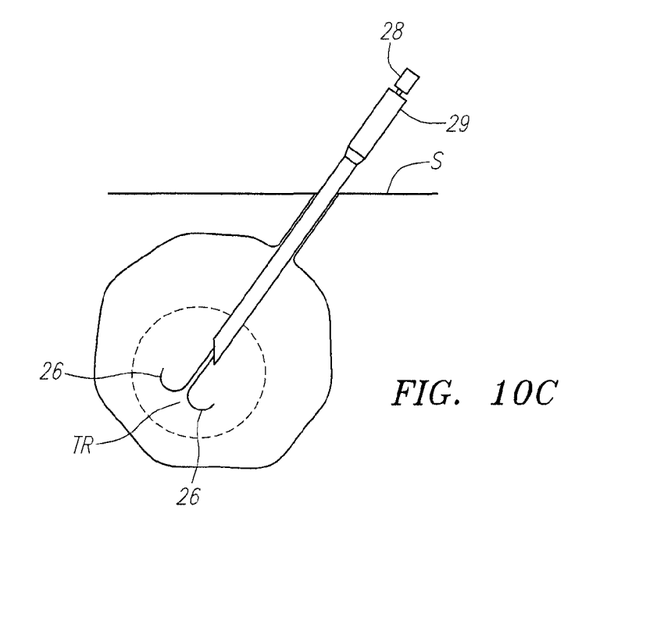

Referring now to FIGS. 10A-10C, the operation of the tissue ablation system 2 is described in treating a treatment region TR within tissue T located beneath the skin or an organ surface S of a patient. The cannula 12 is first introduced within the treatment region TR, so that the distal end 14 of the cannula 12 is located at the target site TS, as shown in FIG. 10A. This can be accomplished using any one of a variety of techniques. In some cases, the cannula 12 and shaft 20 may be introduced to the target site TS percutaneously directly through the patient's skin or through an open surgical incision. In this case, the cannula 12 (or the electrode 92) may have a sharpened tip, e.g., in the form of a needle, to facilitate introduction to the target site TS. In such cases, it is desirable that the cannula 12 be sufficiently rigid, i.e., have a sufficient column strength, so that it can be accurately advanced through tissue T. In other cases, the cannula 12 may be introduced using an internal stylet that is subsequently exchanged for the shaft 20 and electrode array 30. In this latter case, the cannula 12 can be relatively flexible, since the initial column strength will be provided by the stylet. More alternatively, a component or element may be provided for introducing the cannula 12 to the target site TS. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The cannula 12 and shaft 20 can then be introduced through the sheath lumen, so that the distal end 14 of the cannula 12 advances from the sheath to the target site TS.

After the cannula 12 is properly placed, the electrode array 30 is deployed out of the lumen 18 of the cannula 12, as shown in FIG. 10B. Particularly, the electrode array 30 is fully deployed to span at least a portion of the treatment region TR, as shown in FIG. 10C. Alternatively, the needle electrodes 26 may be only partially deployed or deployed incrementally in stages during a procedure. The inventive cross-sectional shape of the needle electrodes 26 prevents, or at least reduces an amount of, bending of the electrodes 26 as the electrodes 26 are being deployed.

Next, the RF generator 6 is then connected to the probe assembly 4 via the electrical connector 38, and the RF generator 6 is operated to deliver ablation energy to the needle electrodes 26 either in a monopolar mode or a bipolar mode. After a desired amount of ablation energy has been delivered, the treatment region TR is necrosed, thereby creating a lesion on the treatment region TR.

In many cases, a single ablation may be sufficient to create a desired lesion. However, if it is desired to perform further ablation to increase the lesion size or to create lesions at different site(s) within the treatment region TR or elsewhere, the needle electrodes 26 may be introduced and deployed at different target site(s), and the same steps discussed previously may be repeated. When a desired lesion at treatment region TR has been created, the needle electrodes 26 are retracted into the lumen 18 of the cannula 12, and the probe assembly 4 is removed from the treatment region TR.

It should be noted that although the electrode 26 has been described with reference to one type of ablation device, in alternative embodiments, any of the embodiments of the electrode 26 described herein can be used with other types of ablation devices, or other ablation devices having different configurations. For example, in other embodiments, the electrode 26 can be attached to a heat generating device, which causes the electrode 26 to heat up during use. In such cases, the electrode 26 is used to deliver ablation energy in a form of heat.

Figure 11:
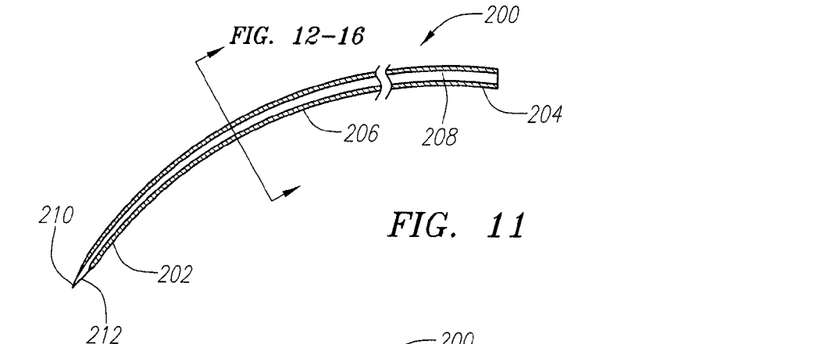
FIG. 11 illustrates a partial side cross-sectional view of a tissue-penetrating element having a lumen in accordance with some embodiments.

In some embodiments, the electrode 26 can further include a lumen for delivering an agent, such as a conductive fluid, during use. FIG. 11 illustrates an electrode 200 having fluid delivery capability in accordance with other embodiments of the invention. The electrode 200 includes a distal end 202, a proximal end 204, and a body 206 extending between the distal and the proximal ends 202, 204. The electrode 200 also includes a sharp distal tip 210 for penetrating tissue. The electrode 200 further includes a lumen 208 located within the body 206, and a distal opening 212 in fluid communication with the lumen 208. The proximal end 204 of the electrode 200 is configured to be coupled to a source (not shown) of conductive fluid. During use, the electrode 200 is deployed within target tissue in a similar manner as that described previously, and conductive fluid is delivered to the target tissue from the source via the lumen 208. The delivered conductive fluid enhances the electrical characteristic of target tissue, thereby allowing the target tissue to be ablated more accurately and efficiently. In other embodiments, instead of using the lumen 208 to deliver conductive fluid, the lumen 208 can be used to deliver other substance, such as cooling fluid to cool the body 206, during use.

Figure 12:
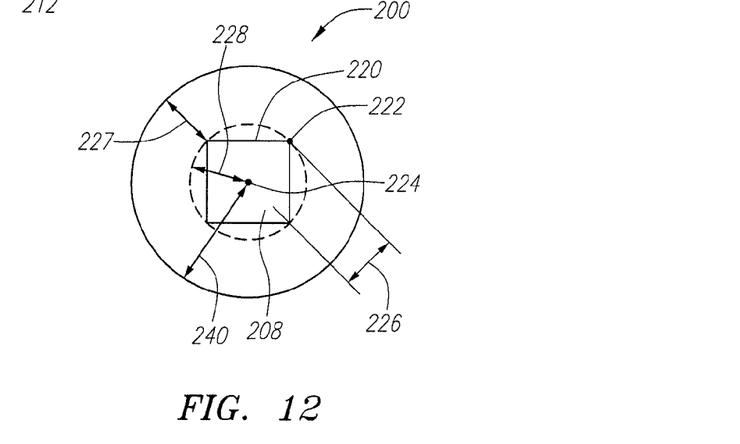
FIG. 12 illustrates a cross-sectional view of the tissue-penetrating element of FIG. 11.

FIG. 12 illustrates a cross-sectional view of the electrode 200 of FIG. 11. As shown in FIG. 12, at least a portion of the body 206 of the electrode 200 has an exterior cross-sectional profile that is circular, while the cross-sectional shape of the interior lumen 208 has a plurality of sides 220. The lumen 208 is sized such that a distance 226 between a point 222 of intersection of two adjacent sides 220 and a center 224 of the lumen 208 is equal to a prescribed radius 228 for the lumen. The square cross-sectional shape of the lumen 208 is advantageous over the circular cross-sectional profile (shown as dotted line) in that the square cross-sectional profile of the lumen 208 provides better cross-sectional property (e.g., I) for the body 206, thereby resulting in the body 206 having a stronger bending stiffness than that of an electrode with a lumen having a circular cross-sectional profile. In other embodiments, the distance 226 can be larger than the prescribed radius 228. For example, the lumen 208 can be sized such that the sides 220 of the lumen 208 are tangential to a circle having the radius 228. In some embodiments, when the square shape (or other polygon shape) is used for the lumen 208, the radius 240 of the electrode 200 can be reduced while achieving a prescribed bending stiffness.

Figure 13:
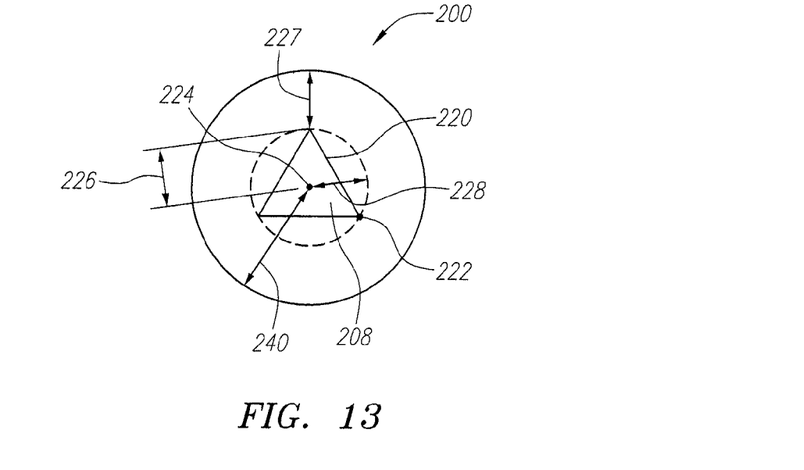
FIGS. 13-16 illustrate alternative cross-sections of the tissue-penetrating elements of FIG. 11.
Figure 14:
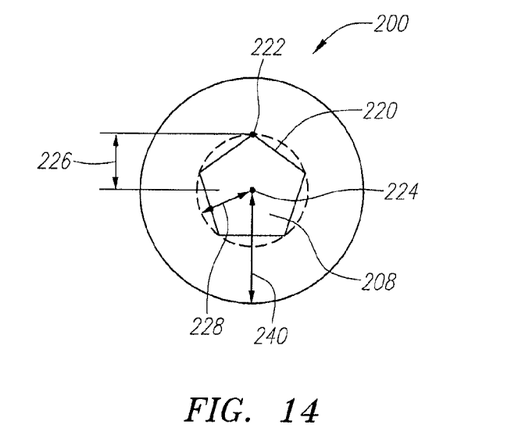
Figures 15, 16:
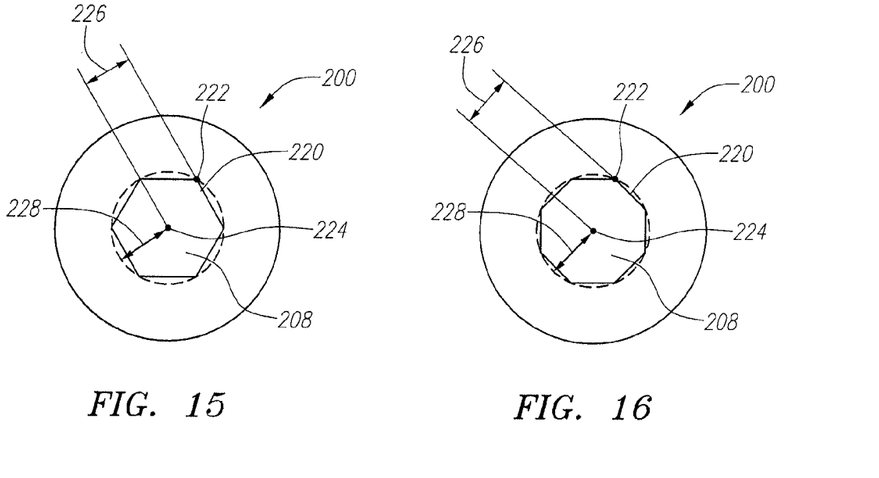

It should be noted that in alternative embodiments, instead of a square profile, the lumen 208 can have other cross-sectional profiles, such as a triangle (FIG. 13), a pentagon (FIG. 14), a hexagon (FIG. 15), and an octagon (FIG. 16). Also, in other embodiments, instead of the exterior circular cross-sectional profile of the body 206 shown, at least a portion of the body 206 along the length of the electrode 200 can have other exterior cross-sectional profiles, such as those described previously in FIGS. 4-9. In any case, the body 206 and the lumen 208 are sized such the electrode 200 has a prescribed bending stiffness. Further, in other embodiments, instead of having the deployed profile shown in FIG. 3, the electrode 200 can have a straight deployed profile, other deployed curvilinear profiles (such as an arc, or a bent), or other customized deployed profiles.

In further embodiments, instead of using the tissue-penetrating element 200 as an electrode, any of the embodiments of the tissue-penetrating element 200 can be used with other types of medical devices. For example, in other embodiments, the tissue-penetrating element 200 can be a component of an agent delivery device (e.g., a needle coupled to a source of agent) or a biopsy device (e.g., a needle coupled to a vacuum source or to a mechanical component).

In some embodiments, instead of, or in addition to, the electrodes having the profiles described previously, the cannula 12 can have any of the cross-sectional shapes of FIGS. 11-16. Such configuration improves a bending stiffness of the cannula 12, thereby allowing a physician to turn or steer the distal end 14 of the cannula 12 by applying a bending force at the proximal end 16. The cannula 12 can have a sharp distal tip for piercing tissue, or alternatively, a blunt tip. In some embodiments, the cannula 12 can be sized such that the cannula 12 has a prescribed bending stiffness. For example, the cannula 12 can be sized to have a prescribed bending stiffness such that, when the distal end 14 of the cannula 12 is within tissue, the cannula 12 does not substantially flex when a physician applies a bending force at the proximal end 16 of the cannula 12. For example, in some embodiments, the cannula 12 can have a wall thickness 227 that is between 0.01 cm and 0.1 cm, and more preferably, between 0.01 cm and 0.03 cm.

It should be noted that although the cannula 12 has been described with reference to an ablation device, in alternative embodiments, the cannula 12 can be a component of other types of medical devices. For example, in other embodiments, the cannula 12 can be attached to a container. In such cases, the cannula 12 is a medical needle configured to deliver a substance, such as drug or diagnostic agent, to a patient. In other cases, the cannula 12 can be configured to extract substance from a site.

Figure 17:
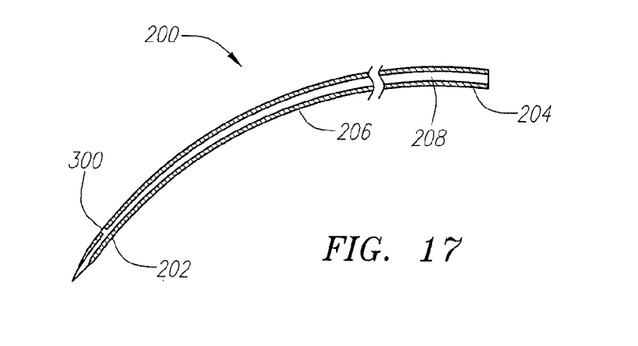
FIG. 17 illustrates a side cross-sectional view of a tissue-penetrating element in accordance with other embodiments, showing the tissue-penetrating element having a side opening.

Although particular embodiments have been shown and described, it should be understood that the above discussion is not intended to limit the present invention to these embodiments. It will be obvious to those skilled in the art that various changes and modifications may be made without departing from the spirit and scope of the present invention. For example, in any of the embodiments described herein, the tissue-penetrating element does not have a sharp tip, and can have a blunt tip instead. Also, in other embodiments, instead of, or in addition to, the distal opening, the tissue-penetrating element can have a side opening 300 (FIG. 17). Thus, the present invention is intended to cover alternatives, modifications, and equivalents that may fall within the spirit and scope of the present invention as defined by the claims.

What is claimed is:

1. A medical device, comprising:
   an elongated probe shaft having a proximal end and a distal end;
   a plurality of needle-shaped electrodes carried by the distal end of the elongated probe shaft, the plurality of needle-shaped electrodes each including a shaft and a fluid delivery lumen extending within the electrode shaft, the electrode shaft having an exterior cross-sectional profile that is polygonal along at least a portion of the electrode shaft length, and the fluid delivery lumen having a circular cross-sectional shape along the entire length of the electrode shaft; and
   a radio frequency generator operatively coupled to the plurality of needle-shaped electrodes.

2. The medical device of claim 1, wherein the portion of the shaft having an exterior cross-sectional profile that is polygonal comprises a square shape.

3. The medical device of claim 2, wherein a distance between a midpoint on a side of the square and a center of the square is between 0.01 cm and 0.5 cm.

4. The medical device of claim 2, wherein a distance between a midpoint on a side of the square and a center of the square is between 0.04 cm and 0.3 cm.

5. The medical device of claim 1, wherein the portion of the shaft having an exterior cross-sectional profile that is polygonal comprises a triangle shape.

6. The medical device of claim 1, wherein the portion of the shaft having an exterior cross-sectional profile that is polygonal comprises a pentagon shape.

7. The medical device of claim 1, wherein the portion of the shaft having an exterior cross-sectional profile that is polygonal comprises a hexagon shape.

8. The medical device of claim 1, wherein the portion of the shaft having an exterior cross-sectional profile that is polygonal comprises an octagon shape.

9. The medical device of claim 1, wherein the plurality of needle-shaped electrodes comprise sharpened tips.

10. The medical device of claim 1, further comprising an elongate cannula having a lumen therein, the probe shaft being slidably disposed within the lumen of the elongate cannula.

11. The medical device of claim 10, wherein the each of the plurality of needle-shaped electrodes are resilient and pre-shaped to radially diverge from one another when deployed out from the lumen of the cannula.

12. The medical device of claim 11, further comprising an electrode disposed on the cannula.

13. The medical device of claim 12, wherein the electrode comprises a tubular electrode.

14. The medical device of claim 12, wherein the electrode disposed on the cannula is a negative electrode and the plurality of needle-shaped electrodes are positive electrodes.

15. The medical device of claim 12, wherein the electrode disposed on the cannula is a positive electrode and the plurality of needle-shaped electrodes are negative electrodes.

* * * * *